(12) United States Patent
Grupp

(10) Patent No.: US 10,937,153 B2
(45) Date of Patent: Mar. 2, 2021

(54) ABSORBENT ARTICLE ANALYSIS FOR HEALTH ASSESSMENT OF PERSONS

(71) Applicant: CRF Box Oy, Helsinki (FI)

(72) Inventor: Jerold Grupp, Holland, PA (US)

(73) Assignee: CRF Box Oy, Helsinki (FI)

( * ) Notice: Subject to any disclaimer, the term of this patent is extended or adjusted under 35 U.S.C. 154(b) by 453 days.

(21) Appl. No.: 15/791,529

(22) Filed: Oct. 24, 2017

(65) Prior Publication Data
US 2018/0114318 A1 Apr. 26, 2018

(30) Foreign Application Priority Data

Oct. 24, 2016 (FI) ...................................... 20165802

(51) Int. Cl.
*G06T 7/00* (2017.01)
*G06T 7/11* (2017.01)
(Continued)

(52) U.S. Cl.
CPC ........ *G06T 7/0012* (2013.01); *A61B 5/02042* (2013.01); *G06T 7/11* (2017.01); *G06T 7/62* (2017.01); *G06T 7/90* (2017.01); *A61B 5/4318* (2013.01); *A61B 5/6802* (2013.01); *A61B 5/6808* (2013.01); *G06T 2207/10024* (2013.01); *G06T 2207/30204* (2013.01)

(58) Field of Classification Search
None
See application file for complete search history.

(56) References Cited

U.S. PATENT DOCUMENTS

2011/0244589 A1\* 10/2011 Klein ..................... G01N 33/52
436/164
2013/0010094 A1\* 1/2013 Satish ....................... G06T 7/62
348/77
(Continued)

FOREIGN PATENT DOCUMENTS

WO 2014209806 A1 12/2014

OTHER PUBLICATIONS

Magnay et al. "A new menstrual pictogram for use with feminine products that contain superabsorbent polymers" Fertility and Serility® vol. 100, No. 6, Dec. 2013. Copyright © 2013 American Society for Reproductive Medicine, Published by Elsevier Inc. http://dx.doi.org/10.1016/j.fertnstert.2013.08.028, 11 pages.
(Continued)

*Primary Examiner* — Nancy Bitar
(74) *Attorney, Agent, or Firm* — Ziegler IP Law Group, LLC

(57) ABSTRACT

A method, system, device and computer program product for analyzing absorbent articles (300) are provided. The method includes receiving an image or data representing an image of an absorbent region (302) of an absorbent article. The absorbent region comprises at least one stain (350) caused by a bodily fluid discharge of a person using the absorbent article. The absorbent region includes at least one reference mark (304). A surface area of the stain (350) is computed using the at least one reference mark (304). The computed surface area of the stain (350) is used to determine a volume of bodily fluid contained in the absorbent article (300). The volume of the bodily fluid is analyzed to assess a measure of the bodily fluid discharge of the person.

17 Claims, 9 Drawing Sheets

(51) Int. Cl.
  *G06T 7/62*    (2017.01)
  *G06T 7/90*    (2017.01)
  *A61B 5/02*    (2006.01)
  *A61B 5/00*    (2006.01)

(56) References Cited

U.S. PATENT DOCUMENTS

| | | | |
|---|---|---|---|
| 2013/0011042 A1* | 1/2013 | Satish | G06T 5/00 |
| | | | 382/134 |
| 2013/0143194 A1* | 6/2013 | Agami | G06T 7/0004 |
| | | | 434/365 |
| 2015/0087935 A1 | 3/2015 | Davis et al. | |
| 2015/0117745 A1 | 4/2015 | Vapa et al. | |
| 2016/0063698 A1* | 3/2016 | Burnett | G06F 19/321 |
| | | | 382/128 |

OTHER PUBLICATIONS

Finnish Patent and Registration Office Search Report, Application No. 20165802, dated Feb. 10, 2017, 1 page.

\* cited by examiner

ABSORBENT ARTICLE ANALYSIS FOR HEALTH ASSESSMENT OF PERSONS

TECHNICAL FIELD

The present application generally relates to assessing health of individuals, and more particularly to analyzing absorbent articles like sanitary napkins, hygiene pads, diapers, etc. to assess health of persons using the absorbent articles.

BACKGROUND

Within a clinical trial, specifically around women's health and menstruation, a measure of change in clinical effect is often measured in the amount of blood, which saturates a sanitary item, such as a sanitary napkin. For example, estimating menstrual blood loss has been known to be an essential indicator of an iron status, work performance, health condition and well-being of a woman.

As the sanitary items are normally disposed of upon being removed from the clothing, it is necessary to capture some measure of the volume of fluid that they contain. As the used sanitary items contain blood, they need to be disposed of immediately, and would otherwise need to be treated as biohazard.

In some example scenarios, a menstrual diary is a commonly used tool to monitor menstrual blood loss (MBL). World Health Organization (WHO) has laid down certain principles to evaluate MBL from menstrual diaries. Such evaluation usually involves a subjective self assessment of the MBL based on counting a number of days of menstruation, a number of sanitary products used, and rating a severity of bleeding on a subjective scale. However clinical studies and practice often require an accurate assessment and quantification of MBL volume.

Some conventional solutions provide a semi-quantitative assessment of the MBL volume by comparing a sanitary item stain with percentages or pictograms from a Pictorial Blood Loss Assessment Chart (PBAC), where a pictogram depicts a sample stain. Such assessment may rely on an estimate by a rater who chooses a pictogram or percentage that closely resembles the stain on the sanitary item. In case the rater is a subject of a clinical trial and has no background or training relevant to estimation, such assessment may be unreliable. Further, such estimate is usually not an accurate quantification of the MBL volume.

Further, some methods may involve measuring the MBL volume based on a weight change of the sanitary item before and after use. Such methods are inherently imprecise as blood fraction accounts for about 30-40% of menstrual fluid and the blood fraction may be highly variable between individuals. Furthermore, some methods may involve a quantitative chemical analysis of a blood content of a used sanitary item. Such methods may have limited application in the clinical practice as they are expensive and may require the subject to collect, store and submit the used sanitary item to a clinical laboratory for analysis, which may be burdensome and even unacceptable to the subject.

SUMMARY

The following presents a simplified summary of the disclosure in order to provide a basic understanding to the reader. This summary is not an extensive overview of the disclosure and it does not identify key/critical elements or delineate the scope of the specification. Its sole purpose is to present a selection of concepts disclosed herein in a simplified form as a prelude to the more detailed description that is presented later.

In an embodiment, a method for analyzing absorbent articles is disclosed. The method includes receiving an image or data representing an image of an absorbent region of an absorbent article. The absorbent region includes at least one stain caused by a bodily fluid discharge of a person using the absorbent article. The absorbent region includes at least one reference mark. The method includes computing a surface area of the at least one stain using the at least one reference mark. The method determines a volume of bodily fluid contained in the absorbent article based on the computed surface area of the at least one stain.

In an embodiment, a system for analyzing absorbent articles is disclosed. The system includes at least one processor and at least one memory comprising computer program code. The at least one memory and the computer program code configured to, with the at least one processor, cause the system to at least receive an image or data representing an image of an absorbent region of an absorbent article. The absorbent region includes at least one stain caused by a bodily fluid discharge of a person using the absorbent article. The absorbent region includes at least one reference mark. The system is further caused to compute a surface area of the at least one stain using the at least one reference mark and determine a volume of bodily fluid contained in the absorbent article based on the computed surface area of the at least one stain.

In an embodiment, an electronic device for analyzing absorbent articles is disclosed. The electronic device includes a display, at least one processor and at least one memory including computer program code corresponding to an absorbent article analysis application configured to facilitate analysis of absorbent articles. The at least one memory and the computer program code are configured to, with the at least one processor, cause the electronic device to at least receive an image or data representing an image of an absorbent region of an absorbent article. The absorbent region includes at least one stain caused by a bodily fluid discharge of a person using the absorbent article. The absorbent region includes at least one reference mark. The electronic device is further caused to compute a surface area of the at least one stain using the at least one reference mark and determine a volume of bodily fluid contained in the absorbent article based on the computed surface area of the at least one stain.

In an embodiment, a computer program product for analyzing absorbent articles is disclosed. The computer program product includes at least one computer-readable storage medium. The computer-readable storage medium includes a set of instructions, which, when executed by one or more processors, cause an electronic device to at least receive an image or data representing an image of an absorbent region of an absorbent article. The absorbent region includes at least one stain caused by a bodily fluid discharge of a person using the absorbent article. The absorbent region includes at least one reference mark. The electronic device is further caused to compute a surface area of the at least one stain using the at least one reference mark and determine a volume of bodily fluid contained in the absorbent article based on the computed surface area of the at least one stain.

Many of the attendant features will be more readily appreciated, as the same becomes better understood by reference to the following detailed description considered in connection with the accompanying drawings.

DESCRIPTION OF THE DRAWINGS

The present description will be better understood from the following detailed description read in light of the following accompanying drawings, wherein.

Like reference numerals are used to designate like parts in the accompanying drawings.

DETAILED DESCRIPTION

Figure 1:
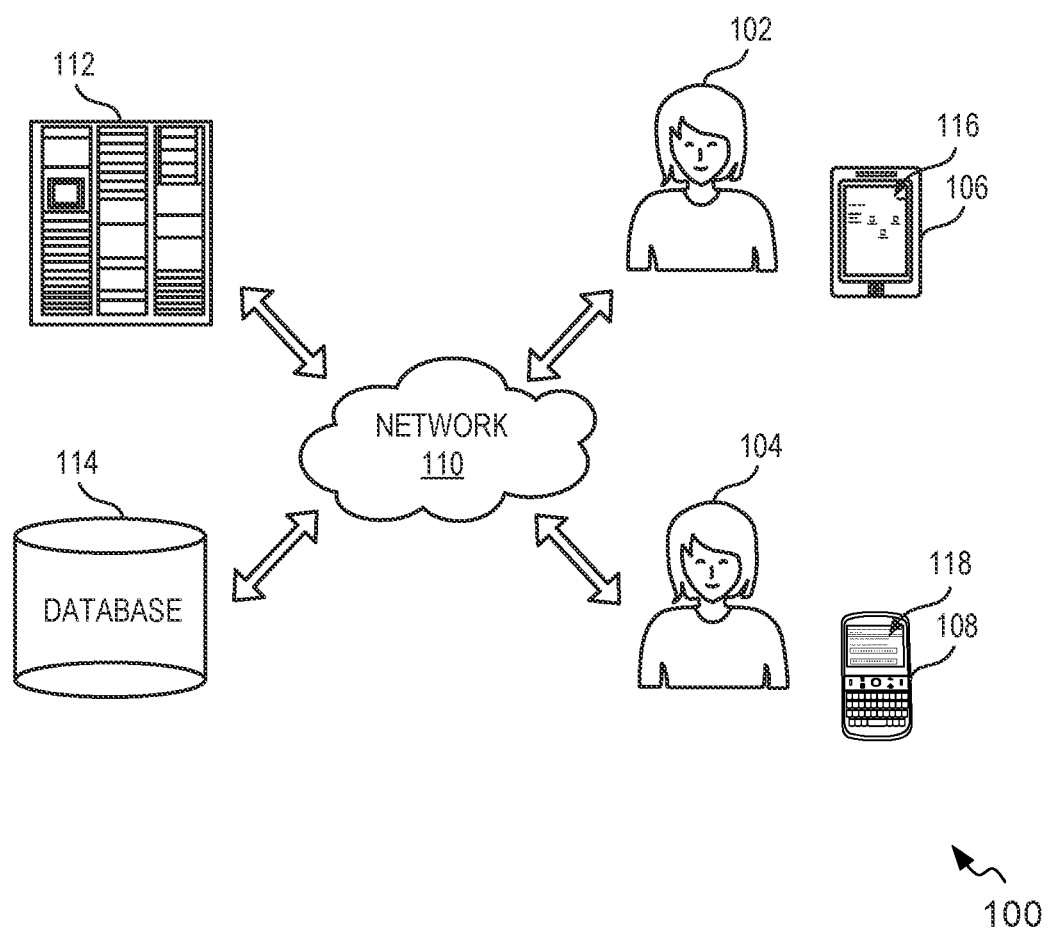
FIG. 1 illustrates an example environment, where various embodiments of the present disclosure may be practiced.

In various embodiments, systems, methods, electronic devices and computer program products for analyzing absorbent articles to estimate bodily fluid discharge of persons using the absorbent articles are provided. The estimation of a bodily fluid discharge from a person may be performed as part of a clinical trial to determine a health status of the person (also referred to as "subject"). In an illustrative example, a woman may use an absorbent article, such as a sanitary napkin, to collect a bodily fluid discharge, such as a menstrual fluid discharge. The absorbent article may be analyzed to estimate a volume of the menstrual fluid. The estimation of the menstrual blood loss may serve as an indicator of a health condition and well-being of the woman.

In at least one embodiment, a subject of the clinical trial or a patient may use an absorbent article to collect bodily fluid discharge. The absorbent article may include an absorbent region configured to absorb the bodily fluid discharge of the subject. Further, the absorbent region also includes one or more reference marks with pre-determined or known surface areas. The subject may use an image capturing device, such as a camera, to capture an image of the absorbent region of the absorbent article, subsequent to the use of the absorbent article. The absorbent region may include one or more stains caused by the bodily fluid discharge of the subject using the absorbent article. A surface area of the stain(s) may be computed by determining a pixel-to area conversation scale based on the number of image pixels configuring the pre-determined surface area of the one or more reference marks in the image or the data representing the image. A volume of the bodily fluid discharge contained in the absorbent article may then be determined using a mathematical product of the computed surface area of the stain and a pre-determined absorption coefficient of the absorbent region.

It is noted that the term 'absorbent article' as used throughout the detailed description refers to a sanitary product capable of being placed in close contact with a body portion of a person and absorbing a bodily fluid discharged from a body of the person. For example, the sanitary product may be placed in an undergarment under a crotch, anal or vaginal area of the person to absorb a bodily fluid discharged from a body of the person. In an illustrative example, the bodily fluid is menstrual fluid, and the absorbent article is one of a feminine hygiene pad, a pantiliner, a sanitary napkin, and a topsheet. In another illustrative example, the bodily fluid is one of urine and an anal exudate, and the absorbent article is one of a diaper, a nappy and an incontinence device. In yet another illustrative example, the bodily fluid is blood and the absorbent article is one of a bandage pad, a first aid bandage and an adhesive bandage.

The various embodiments of the present disclosure are now described in detail using various figures.

It is noted that the detailed description provided below in connection with the appended drawings is intended as a description of the present examples and is not intended to represent the only forms in which the present example may be constructed or utilized. However, the same or equivalent functions and sequences may be accomplished by different examples.

FIG. 1 illustrates an example environment 100, where various embodiments of the present disclosure may be practiced. The environment 100 is depicted to include two persons using absorbent articles, such as a person 102 and a person 104, for illustration purposes. It is noted that the environment 100 may include several such persons using absorbent articles. The persons 102 and 104 may be patients in a treatment facility, such as a clinic or a hospital, or, participants of a clinical trial conducted to assess health of a person by estimating a volume of bodily fluid contained in absorbent articles used by respective persons. The persons, such as the persons 102 and 104, may be positioned in remote locations (for example, a respective home environment) or one or more persons may be present in a clinic/hospital or a facility associated with the clinical trial.

Each person may be associated with an application on an electronic device or with an electronic device capable of facilitating communication with other entities of the environment 100 via the network 110. The application on the electronic device may be a service, e.g., a service for a clinical trial, at which the person is registered. For example, the person 102 is connected to the network 110 via device 106 (exemplarily depicted to be a tablet device), and the person 104 is connected to the network 110 via device 108 (exemplarily depicted to be a smartphone device). The devices 106 and 108 may be connected to the network 110 using, a private network, a public network, a Local Area Network (LAN), a wireless network, a Bluetooth based network, or any such type of network. It may be noted that the devices 106 and 108 may not be limited to the tablet device and the smartphone device, respectively, as shown in the environment 100 and that the devices may connect to the network 110 using various electronic devices. Examples of the devices may include, but are not limited to, laptops, desktops, smart watches, smart televisions, smart devices, wearable devices, and the like. It is noted that the devices may be personal devices of the persons or may be provided to the persons at a clinical trial facility.

The network 110 may be a centralized network or may comprise a plurality of sub-networks that may offer a direct communication between the entities or may offer indirect communication between the entities. Examples of the network 110 may include wireless networks, wired networks, and combinations thereof. Some non-exhaustive examples of wireless networks may include wireless local area networks (WLANs), Bluetooth networks, cellular networks and the like. Some non-exhaustive examples of wired networks may include LANs, Ethernet, Fiber Optic networks and the like. A combination of wired networks and wireless networks may include, for example, the Internet.

The environment 100 is further depicted to include a server 112 and a database 114. In an embodiment, server 112 may maintain an infrastructure for hosting applications, such as for example an absorbent article analysis application (hereinafter referred to as application). Instances of the application, for example application 116 and 118 may be installed on devices 106 and 108, respectively. In one embodiment, the application 116 may differ from the application 118, as different versions of the application may be provisioned based on architecture of different electronic devices. In another embodiment, the application 116 may be similar to application 118 and each may correspond to mere different instances of the application running on different electronic devices.

The various functionalities of the server 112 may be embodied in form of cloud services and/or subscription services. The persons 102, 104 using application 116, 118 respectively may interact with the server 112 and may provide data and receive data from the server 112. Further, devices 106, 108 and server 112 may store data in database 114. The database 114 may be accessed directly or via the network 110.

The server 112 may include one or more processing elements (e.g., computing systems, databases, etc.) to process information received from a person via their respective device and/or the database 114 and to assess a measure of a bodily fluid discharge of a person based on processed information. For example, the application 116 may receive an image or data representing the image (for example, image data in encrypted form), via device 106, of an absorbent region of an absorbent article used by the person 102. The application 116 may analyze the image or the data representing the image to compute a surface area of at least one stain caused on the absorbent region by the bodily fluid discharge from the person 102. Further the application 116 may determine a volume of bodily fluid contained in the absorbent article from the computed surface area of the at least one stain. The computed value of the surface area and the determined measure of the volume of bodily fluid may be sent to the server 112 and/or stored in the database 114. The server 112 may utilize the volume of bodily fluid to assess the measure of bodily fluid discharge of the person 102 and determine, for example, a health status of the person 102.

In an embodiment, the server 112 and the devices 106 and 108 may execute a method for analyzing absorbent articles as described in present disclosure. In another example, server 112 may receive data from devices 106, 108 and performs a part or whole of the method as described in present disclosure. In yet another embodiment, devices 106, 108 perform the whole method as described herein.

A system for analyzing an absorbent article is explained in further detail with reference to FIG. 2.

Figure 2:
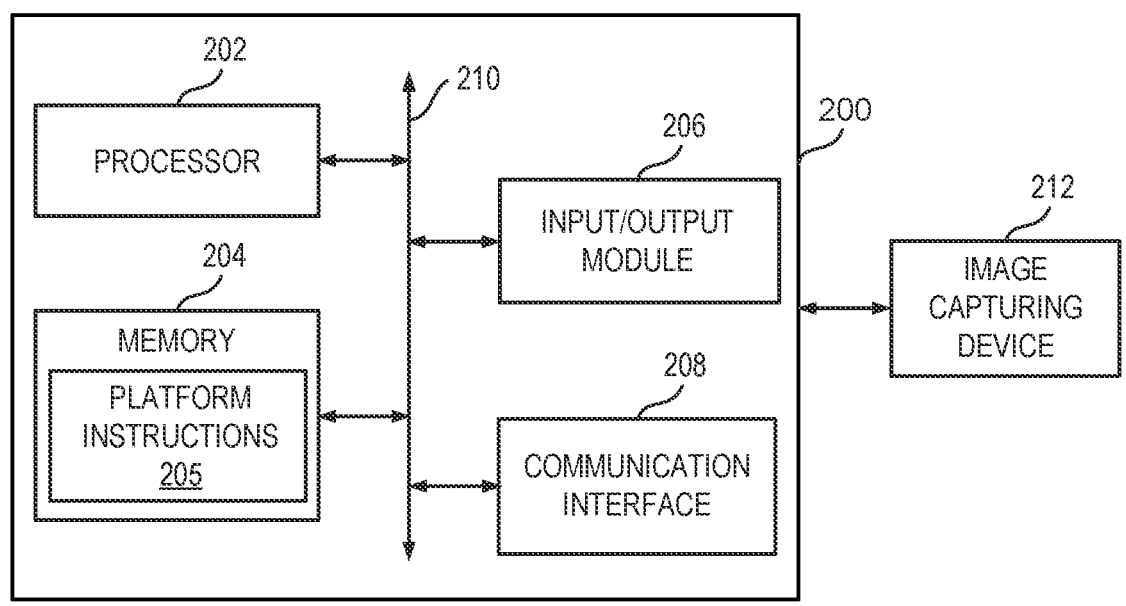
FIG. 2 is a block diagram of a system configured to analyze absorbent articles, in accordance with an example embodiment.

FIG. 2 is a block diagram of a system 200 configured to analyze absorbent articles, in accordance with an example embodiment. The system 200 includes at least one processor such as a processor 202 and at least one memory such as a memory 204. The system 200 also includes an input/output module 206 and a communication interface 208. In at least one example embodiment, one or more components of the system 200 may be included in an electronic device, such as the device 106 (FIG. 1) of the person. Alternatively, the system 200 may embody the electronic device, such as the device 106.

In FIG. 2, the system 200 is depicted to be communicatively associated with an image capturing device 212. An example of the image capturing device 212 may be a camera. The image capturing device 212 may include hardware and/or software necessary for capturing one or more image frames. For example, the image capturing device 212 may include hardware, such as a lens assembly including one or more lens, and, an image sensor. Examples of the image sensor may include, but are not limited to, a complementary metal-oxide semiconductor (CMOS) image sensor, a charge-coupled device (CCD) image sensor, a backside illumination sensor (BSI) and the like.

In some embodiments, the system 200 and the image capturing device 212 may be included within an electronic device. Some non-exhaustive examples of such an electronic device may include a personal computer, a laptop, a tablet computer, a smartphone, a wearable device, a smart device and the like. It is noted that though the image capturing device 212 is depicted to be in communication with the system 200, in some embodiments, the system 200 may be configured to include the image capturing device 212. In some embodiments, the image capturing device 212 may include only the hardware for capturing image frames, while the memory 204 of the system 200 stores instructions for execution by the processor 202 in the form of software for generating an image output. In an example embodiment, the image capturing device 212 may further include a processing element such as a co-processor that assists the processor 202 in processing image frame data and an encoder and/or decoder for compressing and/or decompressing image frame data. The encoder and/or decoder may encode and/or decode according to a standard format, for example, a Joint Photographic Experts Group (JPEG) standard format. In some embodiments, the processor 202 may compress and encrypt the image to configure data representing the image. The compression and/or encryption performed by the processor 202 to configure the data representing the image may be of standard format or of proprietary format.

Although the system 200 is depicted to include only one processor 202, the system 200 may include more number of processors therein. In an embodiment, memory 204 is capable of storing platform instructions 205, where platform instructions 205 are machine executable instructions associated with an absorbent article analysis application configured to facilitate analysis of absorbent articles for estimating a volume of bodily fluid discharge of the person of the absorbent articles. Further, processor 202 is capable of executing the stored platform instructions 205. In an embodiment, the processor 202 may be embodied as a multi-core processor, a single core processor, or a combination of one or more multi-core processors and one or more single core processors. For example, the processor 202 may be embodied as one or more of various processing devices, such as a coprocessor, a microprocessor, a controller, a digital signal processor (DSP), a processing circuitry with or without an accompanying DSP, or various other processing devices including integrated circuits such as, for example, an application specific integrated circuit (ASIC), a field programmable gate array (FPGA), a microcontroller unit (MCU), a hardware accelerator, a special-purpose computer chip, and the like. In an embodiment, the processor 202 may be configured to execute hard-coded functionality. In an embodiment, the processor 202 may be embodied as an executor of software instructions, wherein the software instructions may specifically configure the processor 202 to perform algorithms and/or operations described herein when the software instructions are executed.

The memory 204 may be embodied as one or more volatile memory devices, one or more non-volatile memory devices, and/or a combination of one or more volatile memory devices and non-volatile memory devices. For example, the memory 204 may be embodied as magnetic storage devices (such as hard disk drives, floppy disks, magnetic tapes, etc.), optical magnetic storage devices (e.g., magneto-optical disks), CD-ROM (compact disc read only memory), CD-R (compact disc recordable), CD-R/W (compact disc rewritable), DVD (Digital Versatile Disc), BD (BLU-RAY® Disc), and semiconductor memories (such as mask ROM, PROM (programmable ROM), EPROM (erasable PROM), flash ROM, RAM (random access memory), etc.).

The input/output module 206 (hereinafter I/O module 206) is configured to facilitate provisioning of an output and/or receiving an input. The I/O module 206 is configured to be in communication with processor 202 and memory 204. Examples of the I/O module 206 include, but are not limited to, an input interface and/or an output interface. Examples of the input interface may include, but are not limited to, a keyboard, a mouse, a joystick, a keypad, a touch screen, soft keys, a microphone, and the like. Examples of the output interface may include, but are not limited to, a display such as a light emitting diode display, a thin-film transistor (TFT) display, a liquid crystal display, an active-matrix organic light-emitting diode (AMOLED) display, a microphone, a speaker, a ringer, a vibrator, and the like. In an example embodiment, the processor 202 may include I/O circuitry configured to control at least some functions of one or more elements of I/O module 206, such as, for example, a speaker, a microphone, a display, and/or the like. The processor 202 and/or the I/O circuitry may be configured to control one or more functions of the one or more elements of the I/O module 206 through computer program instructions, for example, software and/or firmware, stored on a memory, for example, the memory 204, and/or the like, accessible to the processor 202.

In an embodiment, the I/O module 206 may be configured to provide a user interface (UI) configured to provide options or any other display to a user of the system 200. In addition, the I/O module 206 may be integrated with mechanisms configured to receive inputs from the user of system 200.

The communication interface 208 enables the system 200 to communicate with other entities over various types of networks such as network 110 as explained with reference to FIG. 1. For example, the communication interface 208 may include transceiver circuitry to receive an instance of the absorbent article analysis application from the server 112 and/or transmit information, such as the computed surface area of the stain and/or the volume of the bodily discharge fluid contained in the absorbent article, to the server 112 for subsequent assessment. The communication interface 208 may also facilitate communication with the image capturing device 212. In scenarios where the image capturing device 212 is included within the system 200, the communication interface 208 may include relevant application programming interfaces (APIs) to facilitate communication with an image processing application associated with the image capturing device 212.

In an embodiment, various components of system 200, such as the processor 202, the memory 204, the I/O module 206 and the communication interface 208 may be configured to communicate with each other via or through a centralized circuit system 210. The centralized circuit system 210 may be various devices configured to, among other things, provide or enable communication between the components (202-208) of the system 200. In certain embodiments, the centralized circuit system 210 may be a central printed circuit board (PCB) such as a motherboard, a main board, a system board, or a logic board. The centralized circuit system 210 may also, or alternatively, include other printed circuit assemblies (PCAs) or communication channel media.

The system 200 as illustrated and hereinafter described is merely illustrative of a system that could benefit from embodiments of the invention and, therefore, should not be taken to limit the scope of the invention. It is noted that the system 200 may include fewer or more components than those depicted in FIG. 2. As explained above, the system 200 may be included within or embody an electronic device. In another embodiment, the system 200 may be a standalone component in a remote machine connected to a communication network (such as the network 110 explained with reference to FIG. 1) and capable of executing a set of instructions (sequential and/or otherwise). Moreover, system 200 may be implemented as a centralized system, or, alternatively, the various components of system 200 may be deployed in a distributed manner while being operatively coupled to each other. In an embodiment, one or more functionalities of system 200 may also be executed by the sever 112.

In at least one example embodiment, the system 200 is caused to receive an image or data representing an image of an absorbent region of an absorbent article. Some non-exhaustive examples of the absorbent article include a sanitary napkin, a feminine hygiene pad, a pantiliner, a topsheet, a diaper, a nappy, an incontinence device and the like. In at least one embodiment, a person of the absorbent article may use the absorbent article to collect bodily fluid discharge. Some non-exhaustive examples of the bodily fluid include menstrual fluid, urine, anal exudate, blood and the like. In an illustrative example, a woman may use an absorbent article, such as a sanitary napkin, to collect a bodily fluid discharge, such as menstrual fluid.

The absorbent article may include an absorbent region configured to absorb the bodily fluid discharge of the person. Further, the absorbent region also includes one or more reference marks with pre-determined or known surface areas. An example absorbent article including an absorbent region and a reference mark is shown in FIG. 3A.

Figure 3A:
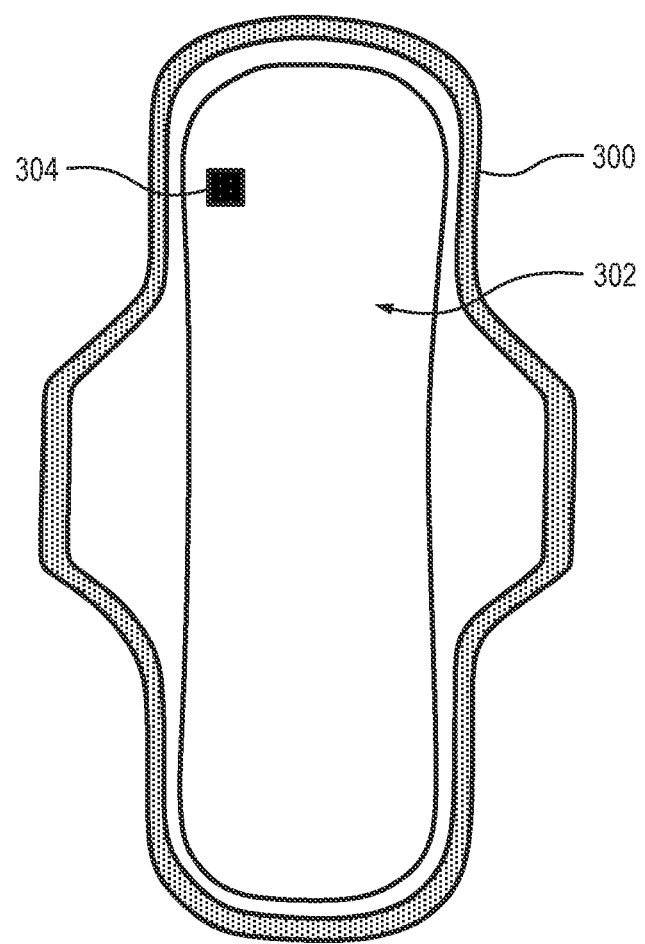
FIG. 3A shows an absorbent article, in accordance with an example embodiment.

FIG. 3A shows an absorbent article 300, in accordance with an example embodiment. The absorbent article 300 is exemplarily depicted to be a sanitary napkin for illustration purposes. The absorbent article 300 includes an absorbent region 302. The absorbent region 302 is associated with a predetermined shape and size and a known absorption coefficient. The absorbent region is configured to be placed in close contact with a body portion of a person and absorb a bodily fluid discharge of the person. In an illustrative example, the absorbent article 300 may be placed in an undergarment under a crotch, anal or vaginal area of the person such that the absorbent region 302 is able to absorb the bodily fluid discharge, such as for example menstrual fluid discharge of the person.

The absorbent region 302 also includes at least one reference mark associated with a pre-determined surface area. In an embodiment, the reference mark may be configured to occupy the pre-determined surface area on the absorbent region 302. Alternatively, in some embodiments, one or more reference marks may be arranged on the absorbent region 302 such that a reference area encompassed between the one or more reference marks corresponds to the pre-determined surface area.

In FIG. 3A, the absorbent region 302 is depicted to include a reference mark 304. The reference mark 304 is depicted to be a colored square for illustration purposes. Indeed, the reference mark may be configured in different shapes and sizes. In an illustrative example, the reference mark is associated with a surface area of 0.5 square centimeters (sq. cm). It is noted that the absorbent region 302 may include more than one reference mark and the sizes and shapes of each reference mark may vary. For example, in some embodiments, the absorbent region 302 may include four reference dots. The four reference dots may be spaced apart from each other, such that they encompass a pre-determined surface area.

As explained with reference to FIG. 2, an absorbent article includes an absorbent region to collect bodily fluid discharge of a person. The absorption of the bodily fluid discharge may result in one or more stains on the absorbent region. The absorbent region 302 including a stain caused by the bodily fluid discharge of the person is depicted in FIG. 3B.

Figure 3B:
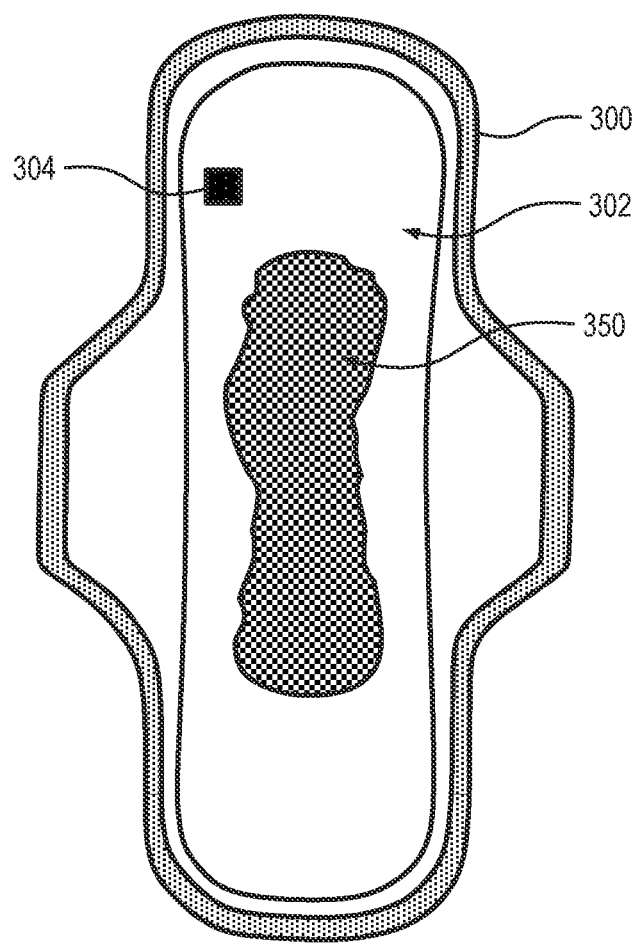
FIG. 3B shows the absorbent article of FIG. 3A bearing a stain caused by the bodily fluid discharge of a person using the absorbent article, in accordance with an example embodiment.

Referring now to FIG. 3B, the absorbent article 300 bearing a stain 350 caused by the bodily fluid discharge of a person using the absorbent article 300 is shown, in accordance with an example embodiment. More specifically, FIG. 3B depicts the stain 350 on the absorbent region 302 of the absorbent article 300 caused by the bodily fluid discharge of the person using the absorbent article 300. It is noted that the absorbent region 302 is depicted to include only one stain for illustration purposes and that the absorbent region 302 may include more than one stain, subsequent to the use of the absorbent article 300 by the person.

Referring now to FIG. 2, in an embodiment, the person may use an image capturing device, such as the image capturing device 212, to capture an image of the absorbent region of the absorbent article, subsequent to the use of the absorbent article.

In at least one example embodiment, the processor 202 of the system 200 is configured to cause display of at least one template in a display panel of the image capturing device 212 to facilitate capturing of the image of the absorbent region. In an embodiment, the memory 204 is configured to store one or more templates to facilitate 'proper' capture of the image of the absorbent region. In some example scenarios, persons may place the image capturing device 212 too close or too far from the absorbent region during image capture. In some other example scenarios, persons may hold the image capturing device 212 at an angle during image capture. In such scenarios, the image captured may be inappropriately zoomed or may be unclear and, as such, may be 'improper' or useless for further analysis. The stored templates may provide the persons with a reference to place the image capturing device during image capture so that the image can be captured with the intended size. One such template is depicted in FIG. 4.

Figure 4:
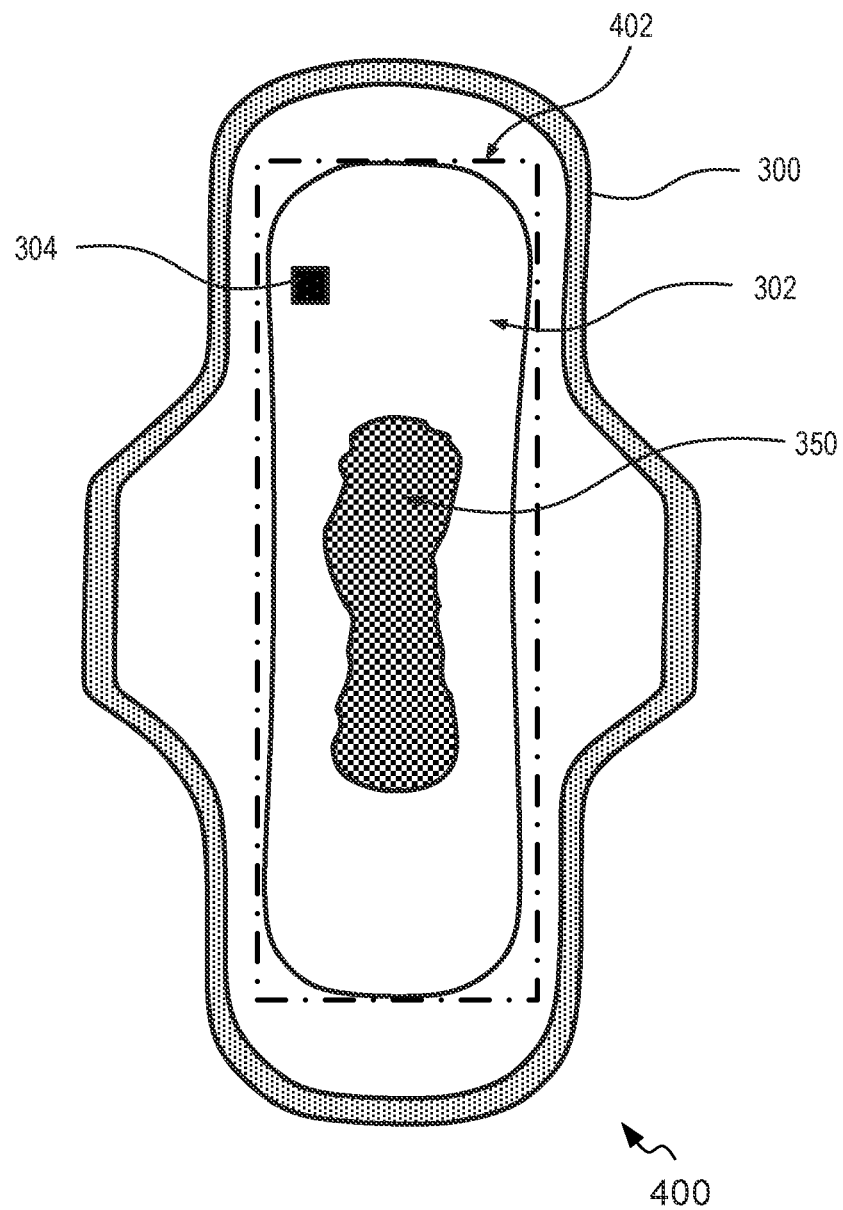
FIG. 4 shows a user interface displayed on a display panel of an image capturing device for illustrating a template configured to facilitate image capture of an absorbent region of the absorbent article, in accordance with an example embodiment.

FIG. 4 shows a user interface (UI) 400 displayed on a display panel of an image capturing device for illustrating a template configured to facilitate image capture of the absorbent region 302 of the absorbent article 300, in accordance with an example embodiment. As explained with reference to FIG. 2, a person using the absorbent article may capture an image of the absorbent region of the absorbent article subsequent to the use of the absorbent article. In order to facilitate the image capture, the processor 202 of the system 200 may cause display of a template, such as the template 402, on the display panel of the image capturing device (not shown in FIG. 4). The template 402 is configured to display an outline comprising boundary portions corresponding to a boundary of the absorbent region 302. The template 402 provides a reference to the person for placing the image capturing device so as to facilitate accurate capture of the image of the absorbent region. More specifically, the template 402 encourages the person to move the image capturing device closer or further until the shape of the absorbent region 302 matches the template 402 shown, and then the image may be captured automatically or manually by the person. The usage of such a template also avoids angles/tilts which would distort the image and might mislead calculations. In some embodiments, edges of the reference mark may be found in the captured image and by applying known trigonometric techniques, a skew of the captured image may be determined. In an event where the skew is greater than a predetermined threshold, for example more than 20 degrees off a perpendicular axis, then an immediate feedback may be provided to the person, so that another image may be captured.

In at least one embodiment, the memory 204 of the system 200 may be configured to store several templates corresponding to several shapes and sizes of the absorbent region. In at least one embodiment, the processor 202 may be configured to select a template from among the plurality of templates based on identification of a type of reference mark and cause display of the template on the display panel of the image capturing device.

It is noted that template 402 displaying an outline of the absorbent region is shown in FIG. 4 for illustration purposes. In some embodiments, the processor 202 may be configured to utilize other templates for facilitating image capture of the absorbent region. Further, it is noted that that the image may be taken from one side (for example, the side with the larger stain) or on both sides of the absorbent region 302. In some scenarios, the persons may be advised to look both at the top of the absorbent article 300 and also to turn it around and look at it from the other side, as the stain may be greater on the bottom portion than on the top portion on account of the absorbent nature of the absorbent region 302. In at least one example embodiment, the image of the absorbent region 302 may be compressed and/or encrypted to configure data representative of the image.

Referring now to FIG. 2, the system 200 may be caused to receive an image or data representing the image of the absorbent region of the absorbent article. As explained above, the absorbent region includes the stain caused by the bodily fluid discharge of the person. In at least one example embodiment, the system 200 is caused to compute a surface area of the stain using the reference mark. More specifically, the processor 202 of the system 200 is configured to compute the surface area of the stain using the reference mark. The computation of the surface area is explained hereinafter.

In an embodiment, the processor 202 of the system 200 is configured to perform a color contrast analysis of the received image or the data representative of the image of the absorbent region to identify a perimeter of the stain. For instance, the processor 202 may be configured to compute Red-Green-Blue (RGB) values of each image pixel in the image (or from the data representing the image) and those image pixels associated with RGB values different than pre-determined RGB values of the absorbent region (for example, RGB values associated with a white color) may be identified. A perimeter of the stain may be determined using the identified pixels associated with different RGB values. In instances where the absorbent region includes more than one stain, the perimeters of individual stains may be identified based on the color contrast analysis and pixel proximity analysis. The perimeter of the stain may facilitate in identification of a number of image pixels corresponding to the stain as will be explained later. In some embodiments, the reference mark arranged on the absorbent region may similarly be identified by comparing RGB values with known RGB values corresponding to the reference mark.

In an embodiment, the processor 202 of the system 200 is caused to identify (1) a first number of pixels representing a reference area indicated by the reference mark in the image or in the data representing the image and (2) a second number of pixels representing the at least one stain in the image or in the data representing the image. In an embodiment, the first number of pixels and the second number of pixels may be identified based on the color contrast analysis. For example, the perimeter of the stain may be used to identify all image pixels corresponding to the stain. The processor 202 may include a counter module configured to count the number of pixels associated with the stain. In an embodiment, the processor 202 is configured to correlate the first number of pixels with the pre-determined surface area of the reference mark to determine a pixel-to-area conversion scale. The processor 202 is further configured to compute the surface area of the stain based on the second number of pixels and the pixel-to-area conversion scale. If an image of the stain is taken on one side (for example, the side with the larger stain) of the absorbent region 302 that stain is used for the computation of the surface area of the stain. If an image of the stain is taken on both sides of the absorbent region 302, the image from the side with the larger stain may be used for the computation of the surface area of the stain. Alternatively, an average of the surface areas of the stains in the images taken from both sides of the absorbent region 302 may be computed. The computation of the surface area of the stain is further explained with reference to an illustrative example in FIG. 5.

Figure 5:
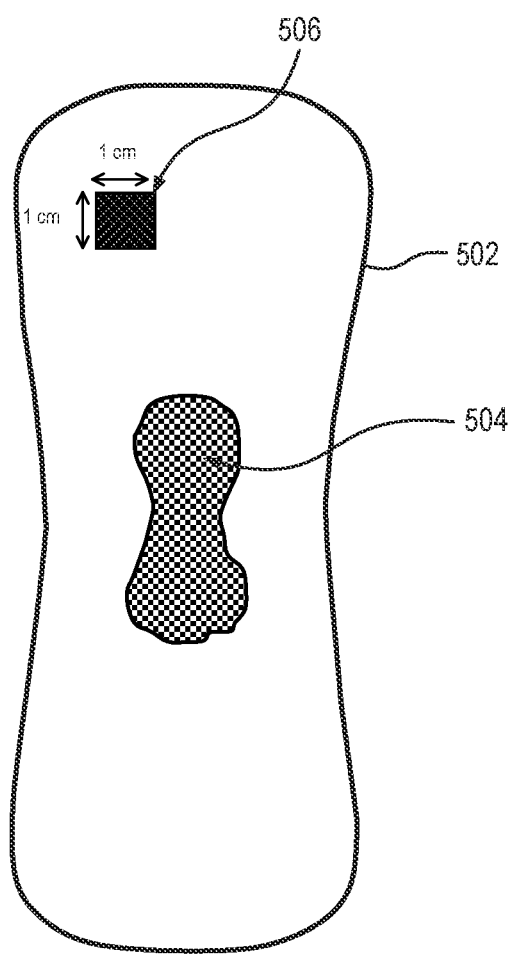
FIG. 5 shows an absorbent region including a stain and a reference mark to illustrate computation of a surface area of the stain, in accordance with an example embodiment.

FIG. 5 shows an absorbent region 502 including a stain 504 and a reference mark 506 to illustrate computation of a surface area of the stain 504, in accordance with an example embodiment. As explained with reference to FIG. 2, the processor 202 is configured to identify a first number of pixels corresponding to the reference mark and a second number of pixels corresponding to the stain. In an illustrative example, the reference mark 506 may be associated with 10000 image pixels and the stain 504 may be associated with 75000 image pixels. The processor 202 may be configured to correlate the first number of pixels (i.e. 10000 image pixels) with the pre-determined surface area of reference mark (for example, one sq. cm) to determine a pixel-to-area conversion scale of 10000:1, implying that one sq. cm of absorbent region corresponds to 10000 image pixels in the image (or in the data representing the image). The processor 202 may then be configured to compute the surface area of the stain 504 using the second number of pixels corresponding to the stain 504 and the pixel-to-area conversion scale. In the current illustrative example, the second number of pixels corresponding to the stain were identified to be 75000 and the pixel-to-area conversion scale was determined to be 10000:1. Accordingly, the processor 202 may be configured to use direct proportion analysis to determine the surface area of the stain 504 to be 7.5 sq. cm based on the second number of pixels and the pixel-to-area conversion.

In at least one example embodiment, the system 200 is caused to determine a volume of bodily fluid contained in the absorbent article based on the computed surface area of the stain. In an illustrative example, the processor 202 may determine the volume of bodily fluid by computing a mathematical product of a pre-determined absorption coefficient of the absorbent region and the computed surface area of the at least one stain. For example, the processor 202 may determine a volume of bodily fluid contained in absorbent article associated with the absorbent region 502 based on the computed surface area (i.e. 7.5 sq. cm) of the stain 504. The volume of bodily fluid may be determined by computing a mathematical product of a pre-determined absorbent coefficient of absorbent region 502 with the computed surface area of stain 504. For example, if the predetermined absorption coefficient of the absorbent region 502 is 0.25 ml/sq. cm, then the volume of bodily fluid contained in a stain of surface area 7.5 sq. cm may be computed as 1.875 ml (0.25 ml/sq. cm*7.5 sq. cm). The computed surface area of stain 504 and the volume of the bodily fluid may be stored in the memory 204 of the system 200.

In at least one example embodiment, the system 200 may be configured to provision the computed surface area of stain and the volume of the bodily fluid to the database 114 (shown in FIG. 1) for storage. Further, in at least one embodiment, the server 112 may be configured to analyze the volume of bodily fluid to assess a measure of the bodily fluid discharge of the person. In an example embodiment, for assessing the measure of the bodily fluid discharge, processor 202 may access the volume of the bodily fluid stored in database 114. In another example, processor 202 may assess the measure of the bodily fluid discharge at the instant the volume of bodily fluid is determined, and store the measure of the bodily discharge and the volume of bodily fluid in database 114 subsequently. In an embodiment, the provisioning of the computed surface area and the volume of bodily fluid to the database 114 and/or the server 112 may be precluded and the system 200 may be configured to analyze the volume of the bodily fluid contained in the absorbent article. In some embodiments, the assessment of patient health and/or health of a subject of the clinical trial may be assessed based on the measure of bodily fluid discharge of the patient/subject.

A method for analyzing absorbent articles is explained hereinafter with reference to FIG. 6.

Figure 6:
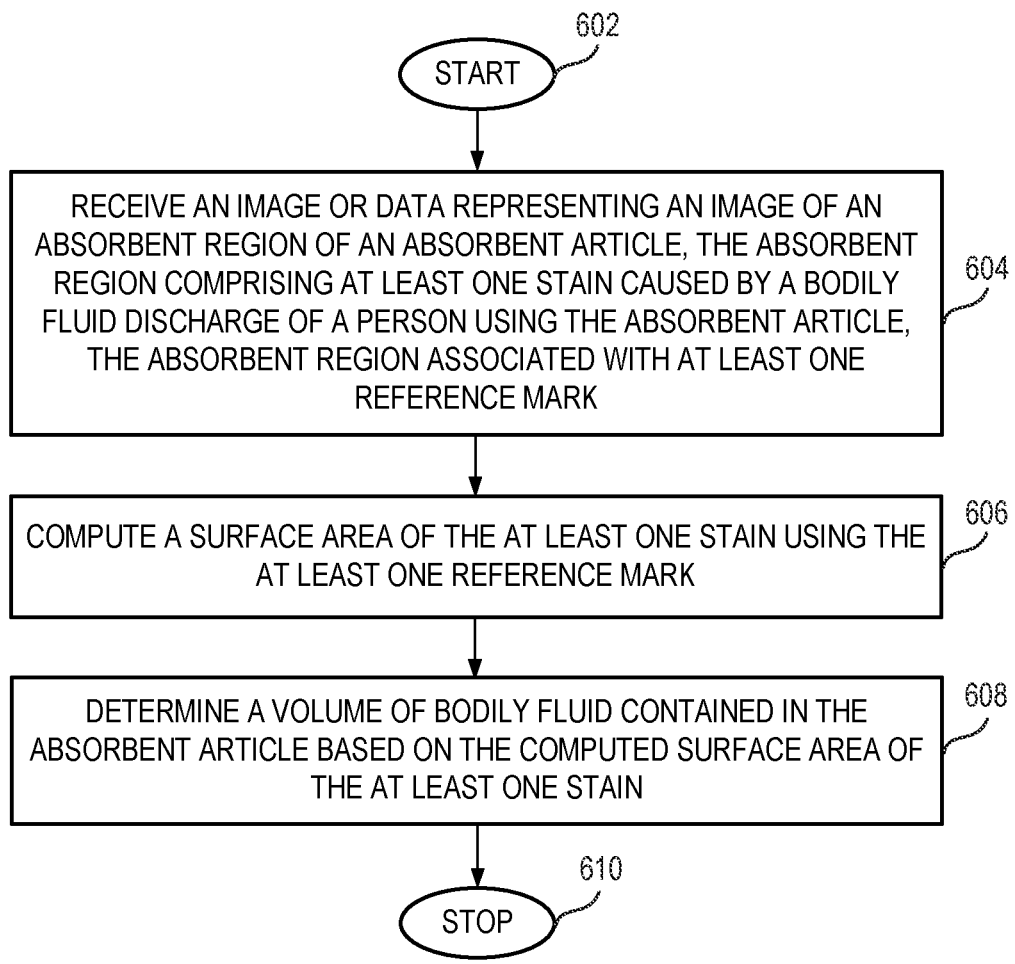
FIG. 6 illustrates an example flow diagram of a method for analyzing an absorbent article, in accordance with an example embodiment.

FIG. 6 illustrates an example flow diagram of a method 600 for analyzing an absorbent article, in accordance with an example embodiment. The method 600 may be performed by the system 200 in combination with the devices 106 and/or 108, database 114 and server 112. The method 600 starts at 602.

At 604 of the method 600, an image or data representing an image of an absorbent region of an absorbent article is received. The absorbent region may include at least one stain caused by the bodily fluid discharge of the person, where the person may use the absorbent article to collect a bodily fluid. For example, the absorbent article may be a sanitary napkin, a feminine hygiene pad, a pantyliner, or a topsheet used to collect the bodily fluid such as menstrual fluid discharged during a menstrual cycle of a person. Further, the absorbent region may be associated with at least one reference mark.

For example, a reference mark may be at least two reference points at a predetermined distance apart, or four dots representing a square of predetermined surface area.

At 606 of the method 600, a surface area of the at least one stain may be computed using the at least one reference mark. The at least one reference mark may be associated with a predetermined surface area. For example, a first number of pixels representing a reference area indicated by the at least one reference area may be identified and correlated with the predetermined surface area to derive a pixel-to-area conversion scale. Further, a second number of pixels representing the surface area of the at least one stain may be identified using a color contrast analysis and may be multiplied with the pixel-to-area conversion scale to compute the surface area of the at least one stain. For example, if a reference area configured by four pixel reference marks indicate a predetermined surface area of one square centimeter (sq. cm.), then the pixel-to-area conversion scale may be computed as 4:1 implying four image pixels per square cm of area of the absorbent region. Further, if 100 pixels are included within a perimeter of a stain, using the pixel-to-area conversion scale of 4:1, the surface area of the stain may be computed by a direct proportion analysis as 25 sq. cm. The computation of the surface area may be performed as explained with reference to FIG. 5 and is not explained herein.

At 608 of the method 600, a volume of the bodily fluid contained in the absorbent article may be determined based on the computed surface area and a predetermined absorption coefficient of the absorbent region. In an illustrative example, the volume of bodily fluid may be determined by computing a mathematical product of a pre-determined absorption coefficient of the absorbent region and the computed surface area of the at least one stain. For example, if the predetermined absorption coefficient of the absorbent region is 0.5 ml/sq. cm, then the volume of bodily fluid contained in a stain of surface area 10 sq. cm may be computed as 5 ml (0.5 ml/sq. cm*10 sq. cm). In at least one example embodiment, a health and well-being of a person may be assessed based on the volume of bodily fluid contained in the absorbent article. The method 600 stops at 610.

Another method for analyzing absorbent articles is explained with reference to FIG. 7.

Figure 7:
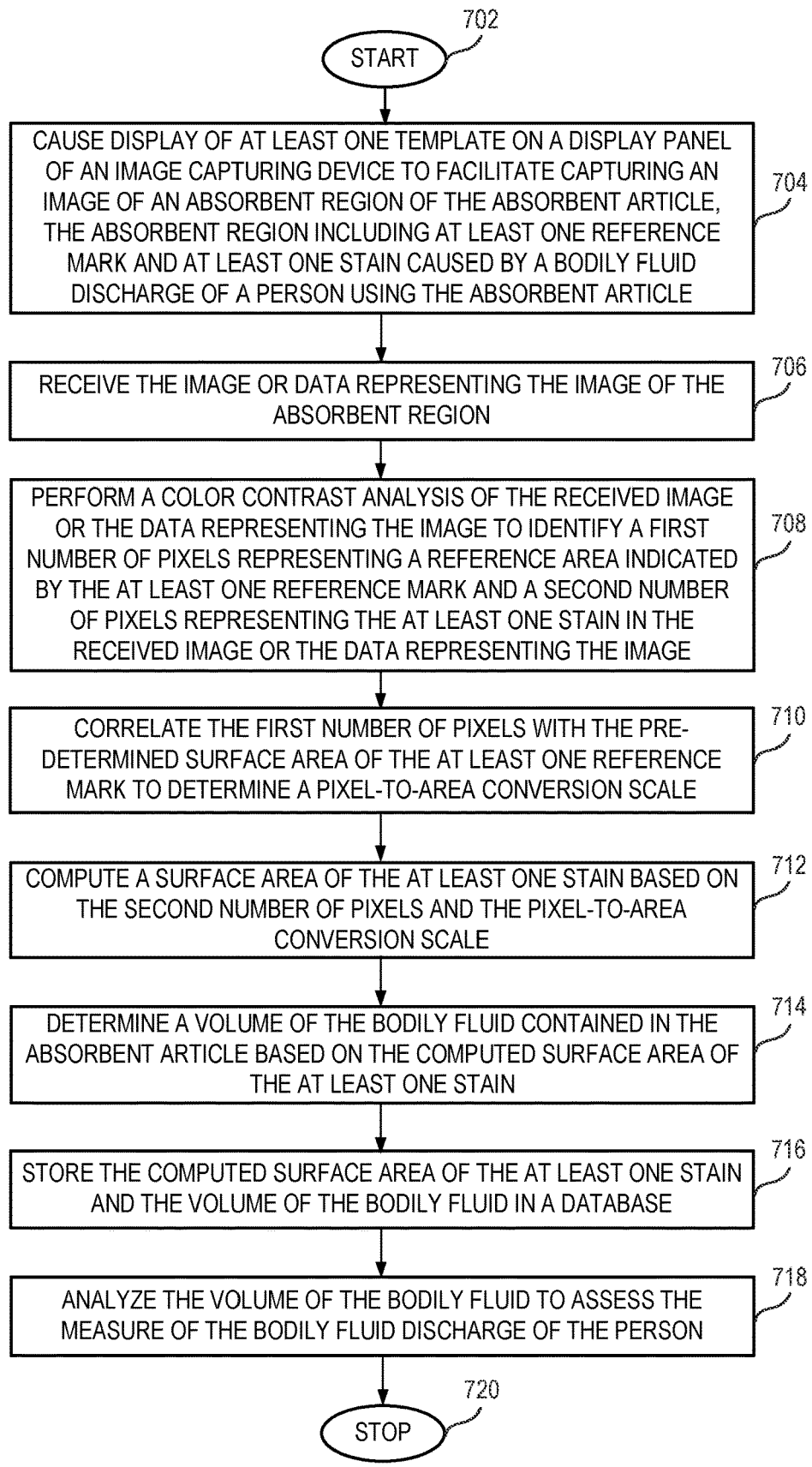
FIG. 7 illustrates an example flow diagram of a method for analyzing an absorbent article, in accordance with an example embodiment.

FIG. 7 illustrates an example flow diagram of a method 700 for analyzing an absorbent article, in accordance with another example embodiment. The method 700 may be performed by the system 200 in combination with the devices 106 and/or 108, database 114 and server 112. The method 700 starts at 702.

At 704 of the method 700, display of at least one template on a display panel of an image-capturing device is caused to facilitate capturing an image of an absorbent region of the absorbent article. The at least one template is indicative of at least one outline of a boundary of the absorbent region. The image may be captured when a shape of the absorbent region matches with a shape of a template from among the at least one template.

The absorbent region includes at least one stain. The at least one stain may be caused by the bodily fluid discharge from the person, where the person may use the absorbent article to collect a bodily fluid that may be discharged from a body of the person. The absorbent region is also associated with at least one reference mark. Further the at least one reference mark is associated with a pre-determined surface area and is printed on the absorbent region.

At 706 of the method 700, the image or data representing the image of the absorbent region including the at least one stain is received.

At 708 of the method 700, a color contrast analysis of the received image or the data representing the image is performed to identify a first number of pixels representing a surface area indicated by the at least one reference mark and a second number of pixels representing the at least one stain in the received image or the data representing the image.

At 710 of the method 700, the first number of pixels is correlated with the pre-determined surface area of the at least one reference mark to determine a pixel-to-area conversion scale.

At 712 of the method 700, a surface area of the at least one stain is computed based on the second number of pixels and the pixel-to-area conversion scale.

At 714 of the method 700, a volume of the bodily fluid contained in the absorbent article is determined based on the computed surface area of the at least one stain. A mathematical product of a predetermined absorption coefficient of the absorption region and the computed surface area of the at least one stain may yield the volume of the bodily fluid contained within the at least one stain and hence within the absorbent article.

At 716 of the method 700, the computed surface area of the at least one stain and the volume of the bodily fluid are stored in a database, for further analysis and records.

At 718 of the method 700, the volume of the bodily fluid is analyzed to assess the measure of the bodily fluid discharge of the person. The method 700 stops at 720.

The disclosed methods 600 and 700 may be implemented using software including computer-executable instructions stored on one or more computer-readable media (e.g., non-transitory computer-readable media, such as one or more optical media discs, volatile memory components (e.g., DRAM or SRAM), or nonvolatile memory or storage components (e.g., hard drives or solid-state nonvolatile memory components, such as Flash memory components) and executed on a computer (e.g., any suitable computer or image processor embedded in a device, such as a laptop computer, net book, web book, tablet computing device, smart phone, or other mobile computing device). Such software may be executed, for example, on a single local computer or in a network environment (e.g., via the Internet, a wide-area network, a local-area network, a remote web-based server, a client-server network (such as a cloud computing network), or other such network) using one or more network computers. Additionally, any of the intermediate or final data created and used during implementation of the disclosed methods or systems may also be stored on one or more computer-readable media (e.g., non-transitory computer-readable media) and are considered to be within the scope of the disclosed technology. Furthermore, any of the software-based embodiments may be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

Figure 8:
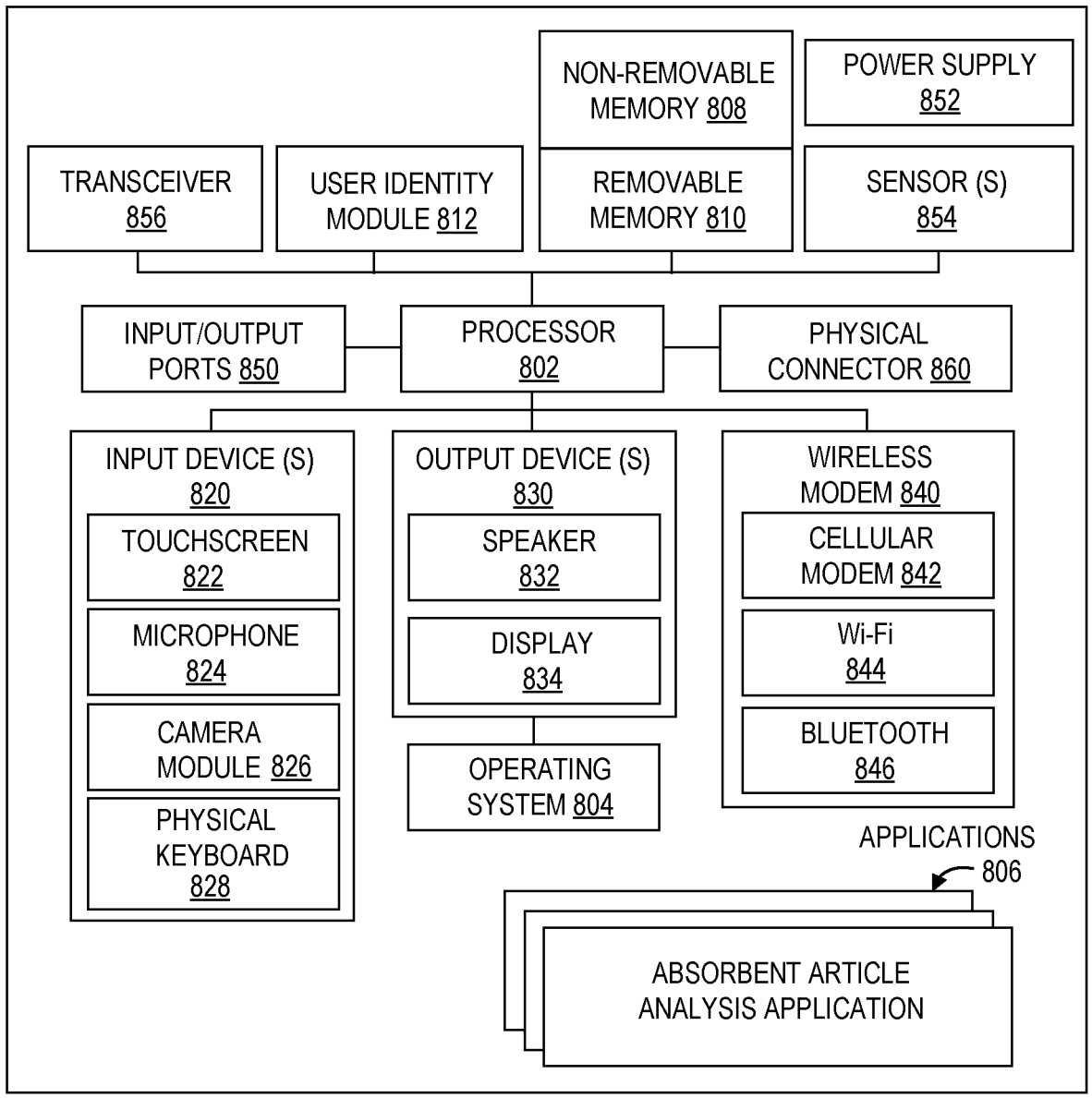
FIG. 8 illustrates an example of an electronic device capable of implementing example embodiments described herein.

Referring now to FIG. 8, a schematic block diagram of a electronic device 800 is shown that is capable of implementing embodiments of techniques for analyzing absorbent articles as described herein. It is noted that the electronic device 800 as illustrated and hereinafter described is merely illustrative of one type of device and should not be taken to limit the scope of the embodiments. As such, it should be appreciated that at least some of the components described below in connection with the electronic device 800 may be optional and thus in an example embodiment may include more, less or different components than those described in connection with the example embodiment of FIG. 8. As such, among other examples, the electronic device 800 could be any of device from among fixed electronic devices, such as desktop computers and electronic kiosks, to mobile electronic devices, such as for example, personal digital assistants (PDAs), mobile televisions, cellular phones, tablet computers, laptops, mobile computers or any combination of the aforementioned, and other types of communication or multimedia devices.

In at least one example embodiment, the electronic device 800 may be a personal electronic device such as a smartphone, a tablet, a personal digital assistant and the like in which an absorbent article analysis application may be installed and running For example, the person may carry the electronic device to a facility, such as for example a hospital, a clinic, or a private washroom area where an image of the absorbent article may be captured and processed. In such a scenario, captured image (or data representing the image) may be received by the absorbent article analysis application and processed via components of the electronic device. In some scenarios, the absorbent article analysis application may be accessed through a web browser installed on the personal electronic device of the person or downloaded through an online application store onto the personal electronic device. Alternatively, in some embodiments, the facility may provide participants of clinical trials with electronic devices pre-installed with the absorbent article analysis applications. In at least one embodiment, the electronic device 800 may correspond to a single purpose device pre-installed with absorbent article analysis application.

It may be noted that the computer program code corresponding to the absorbent article analysis application installed in the electronic device 800 may not only be configured to display one or more user interfaces associated with the absorbent article analysis application, but also cause the electronic device to perform various functionalities associated with analyzing the absorbent articles, such as for example, receiving an image or data representing an image of an absorbent region of an absorbent article, the absorbent region comprising at least one stain caused by a bodily fluid discharge of a person using the absorbent article, the absorbent region associated with at least one reference mark; computing a surface area of the at least one stain using the at least one reference mark; and determining, by the processor, a volume of bodily fluid contained in the absorbent article based on the computed surface area of the at least one stain. The analysis of the absorbent articles for estimating the bodily fluid discharge of the persons using the absorbent articles may be performed by the electronic device 800 as explained with reference to FIGS. 1 to 7 and is not explained again herein.

The illustrated electronic device 800 includes a controller or a processor 802 (e.g., a signal processor, microprocessor, ASIC, or other control and processing logic circuitry) for performing tasks such as signal coding, data processing, image processing, input/output processing, power control, and/or other functions. An operating system 804 controls the allocation and usage of the components of the electronic device 800 and support for one or more applications programs (see, applications 806), such as the absorbent article analysis application, that implements one or more of the innovative features described herein. In addition to absorbent article analysis application, the applications 806 may include common mobile computing applications (e.g., telephony applications, email applications, calendars, contact managers, web browsers, messaging applications) or any other computing application.

The illustrated electronic device 800 includes one or more memory components, for example, a non-removable memory 808 and/or removable memory 810. The non-removable memory 808 can include RAM, ROM, flash memory, a hard disk, or other well-known memory storage technologies. The removable memory 810 can include flash memory, smart cards, or a Subscriber Identity Module (SIM). The one or more memory components can be used for storing data and/or code for running the operating system 804 and the applications 806. Examples of data can include web pages, text, images, sound files, image data, video data, or other data sets to be sent to and/or received from one or more network servers or other devices via one or more wired or wireless networks. The electronic device 800 may further include a user identity module (UIM) 812. The UIM 812 may be a memory device having a processor built in. The UIM 812 may include, for example, a SIM, a universal integrated circuit card (UICC), a universal subscriber identity module (USIM), a removable user identity module (R-UIM), or any other smart card. The UIM 812 typically stores information elements related to a mobile subscriber. The UIM 912 in form of the SIM card is well known in Global System for Mobile Communications (GSM) communication systems, Code Division Multiple Access (CDMA) systems, or with third-generation (3G) wireless communication protocols such as Universal Mobile Telecommunications System (UMTS), CDMA9000, wideband CDMA (WCDMA) and time division-synchronous CDMA (TD-SCDMA).

The electronic device 800 can support one or more input devices 820 and one or more output devices 830. Examples of the input devices 820 may include, but are not limited to, a touch screen 822 (e.g., capable of capturing finger tap inputs, finger gesture inputs, multi-finger tap inputs, multi-finger gesture inputs, or keystroke inputs from a virtual keyboard or keypad), a microphone 824 (e.g., capable of capturing voice input), a camera module 826 (e.g., capable of capturing still picture images and/or video image frames) and a physical keyboard 828. Examples of the output devices 830 may include, but are not limited to a speaker 832 and a display 834. Other possible output devices (not shown) can include piezoelectric or other haptic output devices. Some devices can serve more than one input/output function. For example, the touch screen 822 and the display 834 can be combined into a single input/output device.

In an embodiment, the camera module 826 may include a digital camera capable of facilitating image/video capture. In some implementations, the camera module 826 may include two or more cameras, for example, a front camera and a rear camera positioned on two sides of the electronic device 800. As such, the camera module 826 includes all hardware, such as a lens or other optical component(s), and software for capturing images and/or creating a video stream from a captured video. Alternatively, the camera module 826 may include the hardware needed to view the video, while a memory device of the electronic device 800 stores instructions for execution by the processor 802 in the form of software to create a video stream from a captured video. In an example embodiment, the camera module 826 may further include a processing element such as a co-processor, which assists the processor 802 in processing image frame data and an encoder and/or decoder for compressing and/or decompressing image data. In an embodiment, the camera module 826 may provide live image data (viewfinder image data) to the display 834.

A wireless modem 840 can be coupled to one or more antennas (not shown in FIG. 8) and can support two-way communications between the processor 802 and external devices, as is well known in the art. For example, the communication may include provisioning notifications to the coordinator, establishing a chat link between the participant and the coordinator and the like. The wireless modem 840 is shown generically and can include, for example, a cellular modem 842 for communicating at long range with the mobile communication network, a Wi-Fi-compatible modem 844 for communicating at short range with an external Bluetooth-equipped device or a local wireless data network or router, and/or a Bluetooth-compatible modem 846. The wireless modem 840 is typically configured for communication with one or more cellular networks, such as a GSM network for data and voice communications within a single cellular network, between cellular networks, or between the mobile device and a public switched telephone network (PSTN).

The electronic device 800 can further include one or more input/output ports 850, a power supply 852, one or more sensors 854 for example, an accelerometer, a gyroscope, a compass, or an infrared proximity sensor for detecting the orientation or motion of the electronic device 800, a transceiver 856 (for wirelessly transmitting analog or digital signals) and/or a physical connector 860, which can be a USB port, IEEE 1394 (FireWire) port, and/or RS-232 port. The illustrated components are not required or all-inclusive, as any of the components shown can be deleted and other components can be added.

An embodiment of a method for analyzing absorbent articles comprises receiving, by a processor, an image or data representing an image of an absorbent region of an absorbent article, the absorbent region comprising at least one stain caused by a bodily fluid discharge of a person using the absorbent article, the absorbent region associated with at least one reference mark;

computing, by the processor, a surface area of the at least one stain using the at least one reference mark; and determining, by the processor, a volume of bodily fluid contained in the absorbent article based on the computed surface area of the at least one stain.

In one embodiment of the method, alternatively or additionally, the at least one reference mark is associated with a pre-determined surface area.

In one embodiment, alternatively or additionally, the method further comprises identifying, by the processor, a first number of pixels representing a reference area indicated by the at least one reference mark in the image or the data representing the image;

correlating, by the processor, the first number of pixels with the pre-determined surface area to determine a pixel-to-area conversion scale; and identifying, by the processor, a second number of pixels representing the at least one stain in the image or the data representing the image, wherein the surface area of the at least one stain is computed based on the second number of pixels and the pixel-to-area conversion scale.

In one embodiment, alternatively or additionally, the method further comprises performing, by the processor, a color contrast analysis of the received image or the data representing the image of the absorbent region to identify a perimeter of the at least one stain, wherein the second number of pixels are identified based on the identification of the perimeter of the at least one stain.

In one embodiment, alternatively or additionally, the method further comprises causing, by the processor, display of at least one template in a display panel of an image capturing device to facilitate capturing of the image of the absorbent region. The image is captured when a shape of the absorbent region matches a shape of a template from among the at least one template.

In one embodiment of the method, alternatively or additionally, the template is configured to display an outline comprising at least one boundary portion corresponding to a boundary of the absorbent region.

In one embodiment of the method, alternatively or additionally, the volume of bodily fluid is determined by computing a mathematical product of a pre-determined absorption coefficient of the absorbent region and the computed surface area of the at least one stain.

In one embodiment, alternatively or additionally, the method further comprises storing, by the processor, the surface area of the at least one stain and the volume of bodily fluid in a database.

In one embodiment, alternatively or additionally, the method further comprises analyzing the volume of bodily fluid to assess a measure of the bodily fluid discharge of the person, wherein the person uses the absorbent article to collect the bodily fluid.

In one embodiment of the method, alternatively or additionally, the bodily fluid is a menstrual fluid, and the absorbent article is one of a feminine hygiene pad, a pantiliner, a sanitary napkin, and a topsheet.

In one embodiment of the method, alternatively or additionally, the bodily fluid is one of urine and an anal exudate, and the absorbent article is one of a diaper, a nappy and an incontinence device.

In one embodiment of the method, alternatively or additionally, the bodily fluid is blood and the absorbent article is one of a bandage pad, a first aid bandage and an adhesive bandage.

In one embodiment of the method, alternatively or additionally, the absorbent article comprises one of a feminine hygiene pad, a pantiliner, a sanitary napkin, a topsheet, a diaper, a nappy and an incontinence device.

An embodiment of a system for analyzing absorbent articles comprises at least one processor; and at least one memory comprising computer program code, the at least one memory and the computer program code configured to, with the at least one processor, cause the system to at least perform:

receive an image or data representing an image of an absorbent region of an absorbent article, the absorbent region comprising at least one stain caused by a bodily fluid discharge of a person using the absorbent article, the absorbent region associated with at least one reference mark;

compute a surface area of the at least one stain using the at least one reference mark; and determine a volume of bodily fluid contained in the absorbent article based on the computed surface area of the at least one stain.

In one embodiment of the system, the at least one reference mark is associated with a pre-determined surface area.

In one embodiment, the system is further caused, at least in part to:

identify a first number of pixels representing a reference area indicated by the at least one reference mark in the image or the data representing the image;

correlate the first number of pixels with the pre-determined surface area to determine a pixel-to-area conversion scale; and identify a second number of pixels representing the at least one stain in the image or the data representing the image, wherein the surface area of the at least one stain is computed based on the second number of pixels and the pixel-to-area conversion scale.

In one embodiment, the system is further caused, at least in part to perform a color contrast analysis of the received image or the data representing the image of the absorbent region to identify a perimeter of the at least one stain, wherein the second number of pixels are identified based on the identification of the perimeter of the at least one stain.

In one embodiment, the system is further caused, at least in part to cause display of at least one template in a display panel of an image capturing device to facilitate capturing of the image of the absorbent region, wherein the image is captured when a shape of the absorbent region matches a shape of a template from among the at least one template.

In one embodiment of the system, the template is configured to display an outline comprising at least one boundary portion corresponding to a boundary of the absorbent region.

In one embodiment of the system, the volume of bodily fluid is determined by computing a mathematical product of a pre-determined absorption coefficient of the absorbent region and the computed surface area of the at least one stain.

In one embodiment, the system is further caused, at least in part to store the surface area of the at least one stain and the volume of bodily fluid in a database.

In one embodiment, the system is further caused, at least in part to analyze the volume of bodily fluid to assess a measure of the bodily fluid discharge of the person, wherein the person uses the absorbent article to collect the bodily fluid.

In one embodiment of the system, the absorbent article is one of a feminine hygiene pad, a pantiliner, a sanitary napkin, a topsheet, a diaper, a nappy and an incontinence device.

In one embodiment of the system, the bodily fluid is one of a menstrual fluid, urine, anal exudate and blood.

In one embodiment, the system comprises an image capturing device configured to capture the image of the absorbent region of the absorbent article.

An embodiment of the electronic device comprises
a display;
at least one processor; and
at least one memory comprising computer program code corresponding to an absorbent article analysis application configured to facilitate analysis of absorbent articles, the at least one memory and the computer program code configured to, with the at least one processor, cause the electronic device to at least perform:

receive an image or data representing an image of an absorbent region of an absorbent article, the absorbent region comprising at least one stain caused by a bodily fluid discharge of a person using the absorbent article, the absorbent region associated with at least one reference mark;

compute a surface area of the at least one stain using the at least one reference mark; and determine a volume of bodily fluid contained in the absorbent article based on the computed surface area of the at least one stain.

In one embodiment of the electronic device, the at least one reference mark is associated with a pre-determined surface area.

In one embodiment, the electronic device is further caused, at least in part to:

identify a first number of pixels representing a reference area indicated by the at least one reference mark in the image or the data representing the image;

correlate the first number of pixels with the pre-determined surface area to determine a pixel-to-area conversion scale; and identify a second number of pixels representing the at least one stain in the image or the data representing the image, wherein the surface area of the at least one stain is computed based on the second number of pixels and the pixel-to-area conversion scale.

In one embodiment, the electronic device is further caused, at least in part to perform a color contrast analysis of the received image or the data representing the image of the absorbent region to identify a perimeter of the at least one stain, wherein the second number of pixels are identified based on the identification of the perimeter of the at least one stain.

In one embodiment, the electronic device comprises an image capturing device configured to capture the image of the absorbent region of the absorbent article.

In one embodiment, the electronic device is further caused, at least in part to cause display of at least one template in the display to facilitate capturing of the image of the absorbent region, wherein the image is captured when a shape of the absorbent region matches a shape of a template from among the at least one template.

In one embodiment of the electronic device, the template is configured to display an outline comprising at least one boundary portion corresponding to a boundary of the absorbent region.

In one embodiment of the electronic device, the volume of bodily fluid is determined by computing a mathematical product of a pre-determined absorption coefficient of the absorbent region and the computed surface area of the at least one stain.

In one embodiment of the electronic device, the computed surface area of the at least one stain and the volume of bodily fluid is configured to facilitate analysis of the volume of bodily fluid to assess a measure of the bodily fluid discharge of the person, wherein the person uses the absorbent article to collect the bodily fluid discharge.

In one embodiment of the electronic device, the absorbent article is one of a feminine hygiene pad, a pantiliner, a sanitary napkin, a topsheet, a diaper, a nappy and an incontinence device.

In one embodiment of the electronic device, the bodily fluid is one of a menstrual fluid, urine, anal exudate and blood.

An embodiment of a computer program product comprises at least one computer-readable storage medium, the computer-readable storage medium comprising a set of instructions, which, when executed by one or more processors, cause an electronic device to at least perform:

receive an image or data representing an image of an absorbent region of an absorbent article, the absorbent region comprising at least one stain caused by a bodily fluid discharge of a person using the absorbent article, the absorbent region associated with at least one reference mark;

compute a surface area of the at least one stain using the at least one reference mark; and determine a volume of bodily fluid contained in the absorbent article based on the computed surface area of the at least one stain.

In one embodiment of the computer program product, the at least one reference mark is associated with a pre-determined surface area and electronic device is further caused, at least in part to:

identify a first number of pixels representing a reference area indicated by the at least one reference mark in the image or the data representing the image;

correlate the first number of pixels with the pre-determined surface area to determine a pixel-to-area conversion scale; and identify a second number of pixels representing the at least one stain in the image or the data representing the image, wherein the surface area of the at least one stain is computed based on the second number of pixels and the pixel-to-area conversion scale.

In one embodiment of the computer program product, the electronic device is further caused, at least in part to perform a color contrast analysis of the received image or the data representing the image of the absorbent region to identify a perimeter of the at least one stain, wherein the second number of pixels are identified based on the identification of the perimeter of the at least one stain.

In one embodiment of the computer program product, the electronic device is further caused, at least in part to cause display of at least one template in a display panel of the image capturing device to facilitate capturing of the image of the absorbent region, wherein the image is captured when a shape of the absorbent region matches a shape of a template from among the at least one template.

In one embodiment of the computer program product, the volume of bodily fluid is determined by computing a mathematical product of a pre-determined absorption coefficient of the absorbent region and the computed surface area of the at least one stain.

In one embodiment of the computer program product, the computed surface area of the at least one stain and the volume of bodily fluid is configured to facilitate analysis of the volume of bodily fluid to assess a measure of the bodily fluid discharge of the person, wherein the person uses the absorbent article to collect the bodily fluid discharge.

In one embodiment of the computer program product, the absorbent article is one of a feminine hygiene pad, a pantiliner, a sanitary napkin, a topsheet, a diaper, a nappy and an incontinence device.

In one embodiment of the computer program product, the bodily fluid is one of a menstrual fluid, urine, anal exudate and blood.

Various example embodiments offer, among other benefits, techniques for accurate quantification of bodily fluid discharge. The methods and systems disclosed herein overcome several drawbacks of conventional mechanisms by providing convenience to the person in processing the image on a personal electronic device. Further, disclosed methods and system may improve a reliability factor of the quantification as no estimation is required on behalf of the person during computation of the volume of bodily fluid. Furthermore, as disclosed methods require retention of information such as an area of the at least one stain and the volume of the bodily fluid and not the received image of the absorbent article, privacy and general sensitivity of the person may be safeguarded.

It is noted that various example embodiments as described herein may be implemented in a wide variety of devices, network configurations and applications.

Computer executable instructions may be provided using any computer-readable media that is accessible by computing based device. Computer-readable media may include, for example, computer storage media such as memory and communications media. Computer storage media, such as memory, includes volatile and non-volatile, removable and non-removable media implemented in any method or technology for storage of information such as computer readable instructions, data structures, program modules or the like. Computer storage media includes, but is not limited to, RAM, ROM, EPROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that may be used to store information for access by a computing device. In contrast, communication media may embody computer readable instructions, data structures, program modules, or the like in a modulated data signal, such as a carrier wave, or other transport mechanism. As defined herein, computer storage media does not include communication media. Therefore, a computer storage medium should not be interpreted to be a propagating signal per se. Although the computer storage media is shown within the computing-based device it will be appreciated that the storage may be distributed or located remotely and accessed via a network or other communication link, for example by using communication interface.

The methods described herein may be performed by software in machine readable form on a tangible storage medium e.g. in the form of a computer program comprising computer program code means adapted to perform all the operations of any of the methods described herein when the program is run on a computer and where the computer program may be embodied on a computer readable medium. Examples of tangible storage media include computer storage devices such as disks, thumb drives, memory etc. The software can be suitable for execution on a parallel processor or a serial processor such that the method operations may be carried out in any suitable order, or simultaneously.

Alternatively, or in addition, the functionality described herein (such as the absorbent article analysis instructions) can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), Graphics Processing Units (GPUs). For example, some or all of the device functionality or method sequences may be performed by one or more hardware logic components.

The embodiments illustrated and described herein as well as embodiments not specifically described herein but within the scope of aspects of the invention constitute exemplary system means for managing the electronic informed consent process. For example, the elements illustrated and described with reference to FIGS. 1 and 8, when configured, under control of the processor 202 and program code in the memory 204 to perform the operations illustrated and described with reference to FIGS. 3A, 3B, 4, 5, 6, and 7, constitute an exemplary absorbent article analysis application means for receiving an image of an absorbent region of an absorbent article, the absorbent region comprising at least one stain caused by a bodily fluid discharge of a person using the absorbent article, the absorbent region associated with at least one reference mark; computing a surface area of the at least one stain using the at least one reference mark; and determining a volume of bodily fluid contained in the absorbent article based on the computed surface area of the at least one stain.

The benefits and advantages described above may relate to one embodiment or may relate to several embodiments. The embodiments are not limited to those that solve any or all of the stated problems or those that have any or all of the stated benefits and advantages.

The operations of the methods described herein may be carried out in any suitable order, or simultaneously where appropriate. Additionally, individual blocks may be added or deleted from any of the methods without departing from the spirit and scope of the subject matter described herein. Aspects of any of the examples described above may be combined with aspects of any of the other examples described to form further examples without losing the effect sought.

The above description is given by way of example only and various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the spirit or scope of this specification.

The invention claimed is:

1. A method for analyzing absorbent articles, the method comprising
   causing, by a processor, display of at least one template in a display panel of an image capturing device to facilitate capturing of an image of an absorbent region of an absorbent article,
      the absorbent region comprising at least one stain caused by a bodily fluid discharge of a person using the absorbent article, and the absorbent region includes at least one reference mark having a size and shape,
      the template being for the absorbent region and having a certain shape and size,
      wherein the template is configured to display an outline comprising at least one boundary portion corresponding to a boundary of the absorbent region,
      wherein the image is captured when a shape of the absorbent region matches a shape of a template from among the at least one template,
   receiving, by the processor, the captured image or data representing the image;
   computing, by the processor, a surface area of the at least one stain using the at least one reference mark, wherein the computing is done by identifying a first number of pixels representing a reference area indicated by the reference mark in the image or in the data representing the image and identifying a second number of pixels representing the at least one stain in the image or in the data representing the image; and
   determining, by the processor, a volume of bodily fluid contained in the absorbent article based on the computed surface area of the at least one stain.

2. The method of claim 1, wherein the at least one reference mark is associated with a pre-determined surface area.

3. The method of claim 2, further comprising:
   identifying, by the processor, the first number of pixels representing a reference area indicated by the at least one reference mark in the image or the data representing the image;
   correlating, by the processor, the first number of pixels with the pre-determined surface area to determine a pixel-to-area conversion scale; and
   identifying, by the processor, the second number of pixels representing the at least one stain in the image or the data representing the image, wherein the surface area of the at least one stain is computed based on the second number of pixels and the pixel-to-area conversion scale.

4. The method of claim 3, further comprising:
   performing, by the processor, a color contrast analysis of the received image or the data representing the image of the absorbent region to identify a perimeter of the at least one stain, wherein the second number of pixels are identified based on the identification of the perimeter of the at least one stain.

5. The method of claim 1, wherein the volume of bodily fluid is determined by computing a mathematical product of a pre-determined absorption coefficient of the absorbent region and the computed surface area of the at least one stain.

6. The method of any claim 1, further comprising:
   storing, by the processor, the surface area of the at least one stain and the volume of bodily fluid in a database.

7. The method of claim 1, further comprising:
   analyzing the volume of bodily fluid to assess a measure of the bodily fluid discharge of the person, wherein the person uses the absorbent article to collect the bodily fluid.

8. The method of claim 1, wherein the bodily fluid is a menstrual fluid, and the absorbent article is one of a feminine hygiene pad, a pantiliner, a sanitary napkin, and a topsheet.

9. A system for analyzing absorbent articles, the system comprising:
   at least one processor; and
   at least one memory comprising computer program code, the at least one memory and the computer program code configured to, with the at least one processor, cause the system to at least perform:
   cause, by the at least one processor, display of at least one template in a display panel of an image capturing device to facilitate capturing of an image of an absorbent region of an absorbent article,
      the absorbent region comprising at least one stain caused by a bodily fluid discharge of a person using the absorbent article, and the absorbent region includes at least one reference mark having a size and shape,
      the template being for the absorbent region and having a certain shape and size,
      wherein the template is configured to display an outline comprising at least one boundary portion corresponding to a boundary of the absorbent region,
      wherein the image is captured when a shape of the absorbent region matches a shape of a template from among the at least one template,
   receive the captured image or data representing the image of an absorbent region of an absorbent article, the absorbent region comprising at least one stain caused by a bodily fluid discharge of a person using the absorbent article, and the absorbent region includes at least one reference mark having a size and shape;

compute a surface area of the at least one stain using the at least one reference mark, wherein the computing is done by identifying a first number of pixels representing a reference area indicated by the reference mark in the image or in the data representing the image and identifying a second number of pixels representing the at least one stain in the image or in the data representing the image; and determine a volume of bodily fluid contained in the absorbent article based on the computed surface area of the at least one stain.

10. An electronic device comprising:
a display;
at least one processor; and
at least one memory comprising computer program code corresponding to an absorbent article analysis application configured to facilitate analysis of absorbent articles, the at least one memory and the computer program code configured to, with the at least one processor, cause the electronic device to at least perform:

cause, by the at least one processor, display of at least one template in a display panel of an image capturing device to facilitate capturing of an image of an absorbent region of an absorbent article, the absorbent region comprising at least one stain caused by a bodily fluid discharge of a person using the absorbent article, and the absorbent region includes at least one reference mark having a size and shape, the template being for the absorbent region and having a certain shape and size, wherein the template is configured to display an outline comprising at least one boundary portion corresponding to a boundary of the absorbent region, wherein the image is captured when a shape of the absorbent region matches a shape of a template from among the at least one template, receive the captured image or data representing the image;

compute a surface area of the at least one stain using the at least one reference mark, wherein the computing is done by identifying a first number of pixels representing a reference area indicated by the reference mark in the image or in the data representing the image and identifying a second number of pixels representing the at least one stain in the image or in the data representing the image; and determine a volume of bodily fluid contained in the absorbent article based on the computed surface area of the at least one stain.

11. A computer program product comprising at least one non-transitory computer-readable storage medium, the computer-readable storage medium comprising a set of instructions, which, when executed by one or more processors, cause an electronic device to at least perform:

cause, by the at least one processor, display of at least one template in a display panel of an image capturing device to facilitate capturing of an image of an absorbent region of an absorbent article, the absorbent region comprising at least one stain caused by a bodily fluid discharge of a person using the absorbent article, and the absorbent region includes at least one reference mark having a size and shape, the template being for the absorbent region and having a certain shape and size, wherein the template is configured to display an outline comprising at least one boundary portion corresponding to a boundary of the absorbent region, wherein the image is captured when a shape of the absorbent region matches a shape of a template from among the at least one template, receive the captured image or data representing the image;

compute a surface area of the at least one stain using the at least one reference mark, wherein the computing is done by identifying a first number of pixels representing a reference area indicated by the reference mark in the image or in the data representing the image and identifying a second number of pixels representing the at least one stain in the image or in the data representing the image; and determine a volume of bodily fluid contained in the absorbent article based on the computed surface area of the at least one stain.

12. The computer program product of claim 11, wherein the at least one reference mark is associated with a pre-determined surface area and wherein electronic device is further caused, at least in part to:

correlate the first number of pixels with the pre-determined surface area to determine a pixel-to-area conversion scale; and wherein the surface area of the at least one stain is computed based on the second number of pixels and the pixel-to-area conversion scale.

13. The computer program product of claim 12, wherein the electronic device is further caused, at least in part to:

perform a color contrast analysis of the received image or the data representing the image of the absorbent region to identify a perimeter of the at least one stain, wherein the second number of pixels are identified based on the identification of the perimeter of the at least one stain.

14. The computer program product of claim 11, wherein the volume of bodily fluid is determined by computing a mathematical product of a pre-determined absorption coefficient of the absorbent region and the computed surface area of the at least one stain.

15. The computer program product of claim 11, wherein the computed surface area of the at least one stain and the volume of bodily fluid is configured to facilitate analysis of the volume of bodily fluid to assess a measure of the bodily fluid discharge of the person, wherein the person uses the absorbent article to collect the bodily fluid discharge.

16. The computer program product of claim 11, wherein the absorbent article is one of a feminine hygiene pad, a pantiliner, a sanitary napkin, a topsheet, a diaper, a nappy and an incontinence device.

17. The computer program product of claim 11, wherein the bodily fluid is one of a menstrual fluid, urine, anal exudate and blood.

* * * * *